United States Patent
Hajrovic et al.

(10) Patent No.: US 8,709,360 B2
(45) Date of Patent: Apr. 29, 2014

(54) AUTOMATED PROCESSING MACHINE USED FOR PROCESSING SAMPLES PLACED ON SLIDES AND HAVING AN OUTPUT DEVICE

(75) Inventors: Midhat Hajrovic, Einhausen (DE); Bernhard Neef, Nussloch (DE); Karl-Heinz Westerhoff, Eppingen (DE); Simon Keimer, Leimen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 120 days.

(21) Appl. No.: 13/362,698

(22) Filed: Jan. 31, 2012

(65) Prior Publication Data
US 2012/0192660 A1 Aug. 2, 2012

(30) Foreign Application Priority Data
Jan. 31, 2011 (DE) .................. 10 2011 003 369

(51) Int. Cl.
*A61B 10/00* (2006.01)
(52) U.S. Cl.
USPC ........... 422/536; 422/500; 422/501; 422/502; 422/503; 436/180
(58) Field of Classification Search
USPC ............... 422/536, 64–67, 500–503; 436/180
See application file for complete search history.

(56) References Cited

U.S. PATENT DOCUMENTS

| | | | |
|---|---|---|---|
| 7,603,201 B2 | 10/2009 | Feingold et al. | |
| 7,850,912 B2 | 12/2010 | Favuzzi et al. | |
| 2002/0018733 A1 | 2/2002 | Kapplein et al. | |
| 2002/0051735 A1 | 5/2002 | Dorenkamp et al. | |
| 2002/0054829 A1 | 5/2002 | Dalkidis et al. | |
| 2003/0047863 A1 | 3/2003 | Lang et al. | |
| 2011/0269239 A1* | 11/2011 | Diessel et al. | .................. 436/43 |

FOREIGN PATENT DOCUMENTS

| | | |
|---|---|---|
| DE | 100 10 140 | 9/2001 |
| DE | 100 41 229 | 3/2002 |
| DE | 100 41 230 | 3/2002 |
| DE | 101 44 048 | 3/2003 |
| WO | 2006037332 | 4/2006 |
| WO | 2006098441 | 9/2006 |

OTHER PUBLICATIONS

Search Report issued by the UK Patent Intellectual Property Office in the corresponding GB1122521.6 dated Mar. 26, 2012.

* cited by examiner

*Primary Examiner* — Jyoti Nagpaul
(74) *Attorney, Agent, or Firm* — Schlee IP International, P.C.; Alexander R. Schlee

(57) ABSTRACT

An automated processing machine, in particular an automated coverslipper or an automated stainer used for processing samples placed on slides and having an output device for outputting slides that have been processed by the automated processing machine. The output device includes an extensible and retractable drawer unit. The drawer unit includes at least one receiving channel for receiving a plurality of holders for slides. Holders received in any position in the receiving channel can be removed therefrom when the output device is in the open position. The automated processing machine is designed such that holders intended for output are inserted into the at least one receiving channel.

12 Claims, 3 Drawing Sheets ated processing unit and/or on a portable data carrier or server outside the automated processing machine. Alternatively, only information that indicates where the process data and/or identification information are stored may be stored together.

AUTOMATED PROCESSING MACHINE USED FOR PROCESSING SAMPLES PLACED ON SLIDES AND HAVING AN OUTPUT DEVICE

CROSS-REFERENCE TO RELATED APPLICATION

This application claims the priority of the German patent application DE 102011003369.6 having a filing date of Jan. 31, 2011. The entire content of this prior German patent application DE 102011003369.6 is herewith incorporated by reference.

BACKGROUND OF THE INVENTION

The present invention relates to an automated processing machine used for processing samples placed on slides and having an output device.

The present invention will be described mainly in the context of automated coverslippers, but is basically intended for all automated systems from which holders (called racks) and sample carriers (called "slides") are output.

In histology, samples are processed using various automated processing machines, such as automated stainers (also called histostainers) and automated coverslippers (or in short just coverslippers). An automated stainer is described, for example, in DE 100 41 229 A1. Automated coverslippers are used to coverslip slides carrying, for example, tissue sections. It is known for this purpose to apply a metered amount of a mounting medium (a kind of liquid glue or adhesive) to the slide and subsequently press a cover slip on the slide in order to seal the same. Such an automated glass coverslipper is marketed, for example, by the applicant under the name "Leica CV5030".

After coverslipping, the individual slides are usually sorted into a rack or similar holder. According to the design, this rack may either be the input rack in which the respective slides were introduced into the machine, or a separate output rack. The racks containing the slides that were processed by the automated processing machine are then frequently placed into an output device in the form of a drawer unit from where they can be removed.

However, the conventional output system has certain disadvantages which are sought to be overcome by the present invention.

First of all, the machine is unable to detect whether a rack is actually removed after the drawer is opened. This makes automated processing more complicated, because it is necessary to manually confirm a removal operation. Consequently, it is not possible to automatically monitor (or, in other words, to log) the processing.

Moreover, when the drawer is opened or closed too jerkily or too fast, racks received in the drawer may be caused to slip therein, as a result of which, for example, receiving spaces which are actually free may be blocked, or slides may even slip out of a rack. This occurs especially when more than one rack is removed and, therefore, no hand is free to gently close the drawer. Frequently in such cases, the drawer is ungently pushed closed using other parts of the body.

Moreover, it can happen that the drawer is pulled out while a rack is being placed into the drawer inside the machine, which may even result in damage to the machine and/or to the rack.

It is therefore desirable to provide an improved way of outputting processed slides.

SUMMARY OF THE INVENTION

The present invention proposes automated processing machines for processing samples placed on slides, in particular automated coverslippers or automated stainers, as defined by the features of the independent claims. Advantageous embodiments are the subject matter of the dependent claims and the following description.

According to a first aspect of the present invention, a drawer unit is equipped with at least one receiving channel which operates in the manner of a shift register. Holders intended for output are inserted horizontally into the at least one receiving channel at a certain position, preferably at one end thereof, whereby holders already present in the receiving channel are moved further and/or pushed together. Free positions which may have been left in the at least one receiving channel by the removal of holders are filled again by pushing new holders forward therein. In this manner, an output device is provided which has a large capacity, but yet is particularly easy to fill and empty.

DETAILED DESCRIPTION OF THE INVENTION

In a preferred embodiment, for which separate protection is sought, an automated processing machine according to the present invention includes at least one readout device for reading out at least one identification unit of holders received in the at least one receiving channel. Thus, especially immediately after drawer unit is moved, it is possible to ascertain whether its contents have changed. Once the drawer has been opened and closed, it may be assumed that at least one holder has been removed. If the number of identification units detected after the drawer is closed is the same as before, then no holder has been removed. Consequently, it is always known which positions are occupied and which are free, and also which and when holders were removed from the machine. This allows continuous monitoring of the process chain which, for example in the case of an automated coverslipper, starts with the insertion, followed by coverslipping, drying and possibly additional steps, and ends with the output operation. It is advantageous for the holders present in the output device to be graphically presented to the user on a presentation device, such as a display. In the event that process faults are detected (e.g., temperature out of range in the drying area, incorrect quantity of mounting medium, etc.), it is convenient to highlight this holder clearly visibly in the display representation and to alert the user accordingly during the removal process. The error event can be stored and used for later analysis. This makes it possible to increase the reliability of the overall process.

Holders which are particularly suitable for use in an automated processing machine according to the present invention are those described for example in document DE 100 10 140 A1. Such holders have one or two identification units preferably including RFID transponders. Preferably, at least one of the identification units provides identifications of the slides contained in the holder and/or of a treatment in an automated stainer or coverslipper, as is also described in DE 100 10 140 A1. This feature allows monitoring of holders and slides to be output. Particularly advantageously, such information may be used to uniquely identify the holder. This makes it possible to keep a log of the holder and the slides held therein. This feature is advantageous in particular in the medical field, because it provides a way to track what happened to the holder and slides, and when and where it happened. Therefore, the automated processing machine, here, in particular, a control unit, is preferably adapted such that a process performed on a received slide and identification information stored in an identification unit of the holder holding the slide are stored together, preferably within the automated processing machine, in an attached processing unit and/or in an identification unit of the holder holding the slide. In this manner, a log function can be created in a simple way.

In accordance with a preferred embodiment, the readout device is an RFID reader device or an RFID reader/writer device. RFID transponders are available as very small units, so that they can be incorporated into the holder without making it heavier or changing its shape. Another reason for the use of RFID transponders lies in the low manufacturing and procurement costs and in their ruggedness and reliability, which enhances applicability, in particular, in the medical field, where chemicals and the like are frequently used.

If the at least one readout device is disposed such that holders received in the receiving channel are moved past the readout device as the drawer unit is moved in and out, the number of readout devices required can be kept low and independent of the capacity of the receiving channel.

In accordance with another preferred embodiment, for which separate protection is sought, the output of processed slides is automated in such a way that it can be performed without the problems described at the outset. This is achieved, firstly, by motorizing the output device so that the drawer is moved in and out by a motor upon request of the user. To this end, the user operates a corresponding control means, such as a push button or a key. Within the scope of the present invention, the speed, acceleration and jerk of the drawer movement can be controlled in such a way that, for example, holders received in the drawer are prevented from slipping therein. Secondly, a control unit is provided and preferably programmed to allow the drawer to be moved in and/or out only at appropriate times. Thus, the drawer is prevented from being moved at inappropriate times. The user can remove one or more holders from the machine simultaneously and yet relatively easily cause the drawer to close, even without a free hand, as the case may be.

Advantageously, an indicator means is provided which is adapted to indicate appropriate and/or inappropriate points in time. If the time is not appropriate, the output device will not respond to operation of the control means by moving the drawer unit in or out. In such a case, preferably, the indicator means is controlled to indicate to the user that the drawer unit is currently blocked. In this manner, the user is informed that his control command has been detected, but can currently not be executed. This prevents the user from assuming that the control command has not been detected and/or that the machine is defective. The indicator means may preferably be designed similar to a traffic light with a green light for "drawer unit free" and a red light for "drawer unit blocked". The indicator means may have one element for multiple colors or, alternatively, multiple elements for one color, respectively. The indicator means may also include a display for displaying freely definable texts, symbols, pictograms, pictures, etc.

Further advantages and embodiments of the present invention will become apparent from the description and the accompanying drawings.

It will be understood that the aforementioned features and those described below can be used not only in the specified combinations, but also in other combinations or alone without departing from the scope of the present invention.

The present invention is schematically illustrated in the drawings using an exemplary embodiment, and will be described below in detail with reference to the drawings.

DETAILED DESCRIPTION OF THE DRAWINGS

Figure 1:
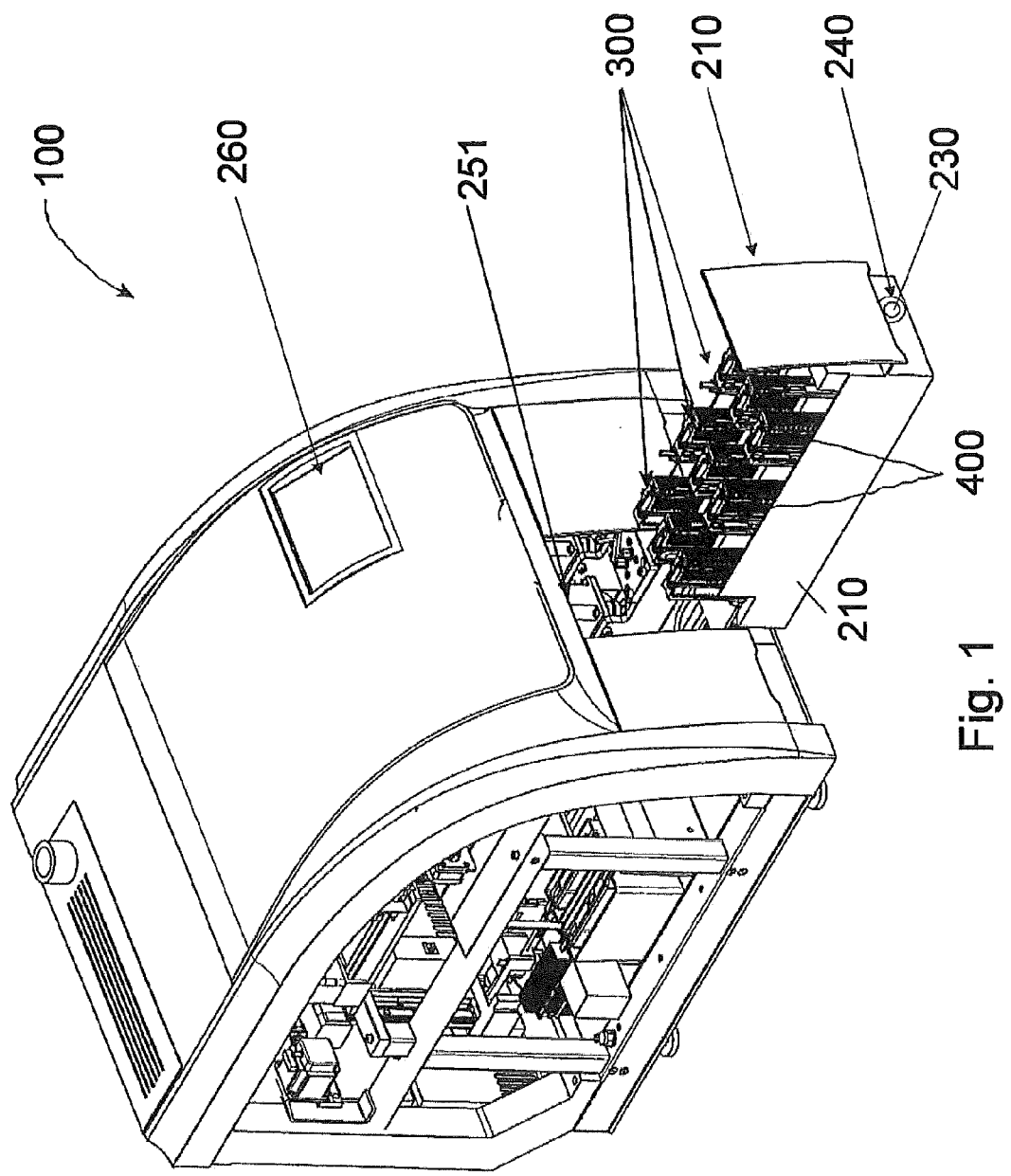
FIG. 1 is a schematic view of a preferred embodiment of an automated processing machine according to the present invention.

In FIG. 1, a preferred embodiment of an automated processing machine according to the present invention, here in the form of an automated glass coverslipper (hereinafter referred to as coverslipper), is shown in schematic perspective view and generally designated 100. The coverslipper is shown without the side wall.

Coverslipper 100 is used to coverslip samples placed on slides. To this end, a mounting medium or adhesive is applied to the slides and then a coverslip is placed on top. This can be done using a coverslipper, as described, for example, in DE 101 44 048 A1.

Further, coverslipper 100 is provided with an output device 200 which, in turn, includes an extensible and retractable drawer unit 210 which, in the present example, has three receiving channels 211, 212 and 213 provided therein. Receiving channels 211, 212 and 213 each serve to receive three holders. In the example shown, three holders 300 are received in each of receiving channels 211, 212 and 213.

Figure 2:
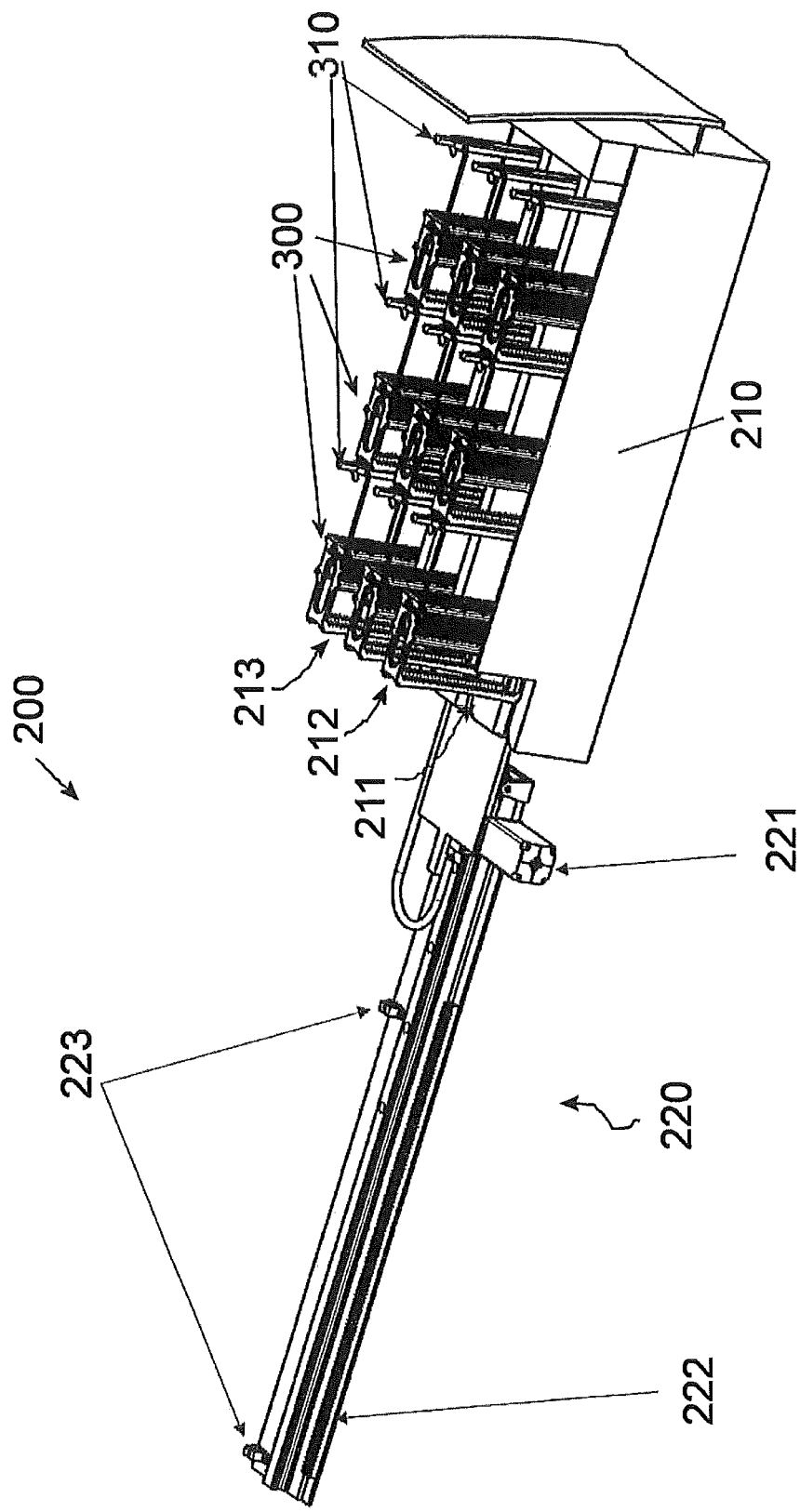
FIG. 2 is a schematic view of an output device of the automated processing machine shown in FIG. 1.

Each of holders 300 holds a number of slides 400 (not shown in FIG. 2), which typically have coverslipped tissue sections thereon. Moreover, holders 300, which are located in brackets 310, are each equipped with one or two RFID transponders containing information. Holders 300 are inserted into receiving channels 211, 212 and 213 with the brackets 310 closed, so that slides 400 cannot fall out of the holders, even when removed without care.

Output device 200 further includes an electric drive 220 including an electric motor 221 and an associated linear guide 222. Electric motor 221 is embodied as a stepper motor and allows drawer unit 210 to move in and out along linear guide 222. The end positions can be monitored by sensors 223. Electric drive 220, and more particularly electric motor 221, is controlled by a control unit (not shown). The control unit is disposed within the coverslipper 100 and suitably programmed to control all functions of coverslipper 100.

Moreover, output device 200 is equipped with a control means, which here takes the form of a key 230 connected to the control unit such that operation of key 230 causes drawer unit 210 to move in or out. In the preferred embodiment shown here, key 230 is surrounded by an indicator means in the form of a light-emitting ring 240 which lights up in different colors, depending on the status of output device 200. Preferably, the light-emitting ring is adapted to light up in green when drawer unit 210 can be caused to move in or out by operating key 230. Further, light-emitting ring 240 is adapted to light up in red when the time is not appropriate and, therefore, the control unit blocks drawer unit 210 from moving in and out. In such a case, operation of key 230 does not cause drawer unit 210 to move in or out.

The control unit is aware of the processing steps taking place in coverslipper 100, which enables it, in particular, to determine appropriate times at which drawer unit 210 can be moved in or out. For example, a point in time is not appropriate, in particular, when a holder 300 is being inserted into one of receiving channels 211-213 while the drawer unit is in the closed position. A point in time may also be inappropriate when other processes take place in coverslipper 100 during which drawer unit 210 should not be opened. Examples of such processes include (automatic) cleaning and/or disinfecting processes.

In the preferred embodiment shown here, output device 200 includes a readout device 251 which is mounted stationary with respect to coverslipper 100 and here includes one or more RFID reader devices. In the present example, readout device 251 is so disposed that when drawer unit 210 is moved in or out, holders 300 received in receiving channels 211-213 are moved past readout device 251 in such a way that readout device 251 can read out at least one RFID transponder of each holder 300. In this manner, it is possible to indicate to the control unit in the automated processing machine whether holders are present in a receiving channel and, if so, where such holders are located. Based on the information stored in the RFID transponders, it is possible to log the processing operations performed and/or the output.

Receiving channels 211-213 operate in the manner of a shift register; it being possible to remove (vertically) any one or more of holders 300 from receiving channels 211-213 when output device 200 is in the open position. As explained earlier, as output device 200 is closed, coverslipper 100, and more particularly its control unit, detects whether any of holders 300 have been removed and, if so, which ones have been removed. The resulting free spaces in receiving channels 211-213 are filled by horizontally advancing holders 300 from inside coverslipper 100 within the receiving channels. There is no need for complex insertion devices ("crane").

Coverslipper 100 has a display 260 for displaying to the user, for example, the status of the output device and/or of holders 300 received therein. If, for example, processing errors are detected, the affected holders are highlighted in the display representation and the user is alerted accordingly during the removal process. The error event is also stored in the log.

Figure 3:
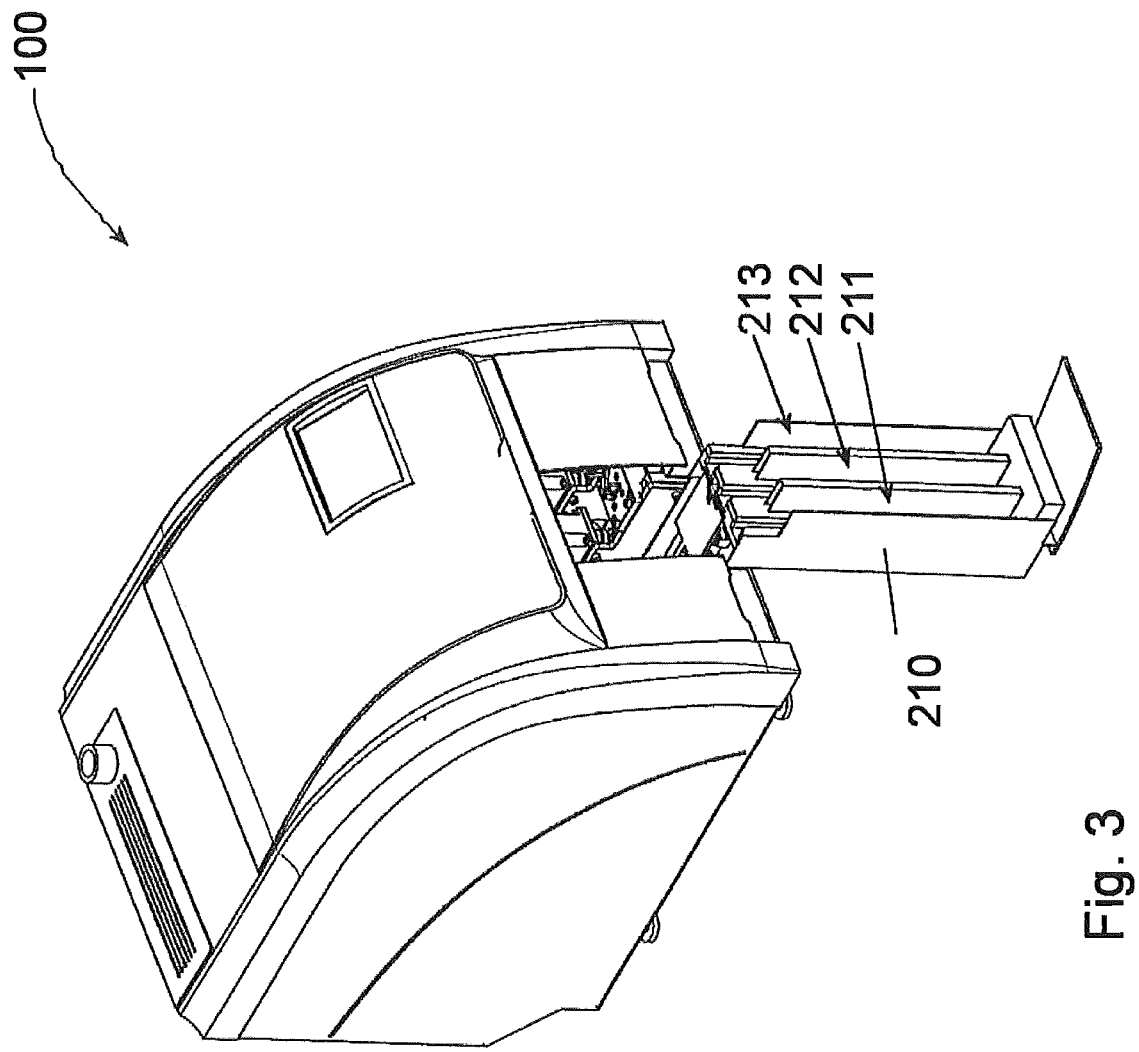
FIG. 3 is a view showing the automated processing machine of FIG. 1 with the output device folded away.

As can be appreciated in FIG. 3, drawer unit 210 of output device 200 can be folded away, and here more particularly folded down. This facilitates access to the interior of the machine and, in particular, to regions located deep inside the machine.

This embodiment also facilitates handling in fault conditions, such as a power failure. This ensures that in the event of a fault, all holders currently in the process can be immediately removed from the machine. To ensure this, once drawer unit 210 of output device 200 has been moved out, it can be released and folded down. This significantly increases the access opening for the user, and also considerably facilitates the removal of racks. Moreover, when the drawer unit is folded down, it does not obstruct the area in front of the machine. Advantageously, even if the drawer unit is motorized, an emergency operation mode allows it to be moved out manually.

What is claimed is:

1. An automated processing machine in one of an automated coverslipper and an automated stainer for processing samples placed on slides; said automated processing machine comprising an output device for outputting slides that have been processed by the automated processing machine, said output device including an extensible and retractable drawer unit so that the output device assumes its open position with the drawer unit extended and its closed position with the drawer unit retracted; wherein
    the drawer unit includes at least one receiving channel for receiving a plurality of holders for slides;
    holders received in any position in the at least one receiving channel are removable from that at least one receiving channel when the output device is in the open position;
    the automated processing machine is designed such that holders intended for output are horizontally inserted into the at least one receiving channel;
    an electric drive is provided for moving the drawer unit in and out;
    a control unit is provided for controlling the electric drive;
    an input element is connected to the control unit for inputting commands causing the drawer unit to move in or out; and
    the control unit is configured to allow the drawer unit to be moved in or out only at appropriate points in time.

2. The automated processing machine as recited in claim 1, comprising at least one readout device that is positioned such that it can read out at least one identification unit of holders received in the at least one receiving channel.

3. The automated processing machine as recited in claim 2, wherein the at least one readout device is positioned such that it can read out at least one identification unit of each of the holders received in the at least one receiving channel.

4. The automated processing machine as recited in claim 2, wherein the at least one readout device is positioned such that holders received in the receiving channel are moved past the readout device as the drawer unit is moved in and out.

5. The automated processing machine as recited in claim 2, wherein the automated processing machine is adapted for storing together a process performed on a received slide and identification information stored in an identification unit of the holder holding the slide.

6. The automated processing machine as recited in claim 2, wherein the at least one readout device is an RFID reader device or an RFID reader/writer device.

7. The automated processing machine as recited in claim 1, comprising an indicator element adapted to indicate at least one of appropriate and inappropriate points in time.

8. The automated processing machine as recited in claim 7, wherein the indicator element includes at least one of a first light-emitting element that lights up to indicate an appropriate point in time and a second light-emitting element that lights up to indicate an inappropriate point in time.

9. The automated processing machine as recited in claim 1, wherein the drawer unit can be folded away.

10. The automated processing machine as recited in claim 9, wherein the drawer unit can be folded away once it has been moved out.

11. An automated processing machine in one of an automated coverslipper and an automated stainer for processing samples placed on slides; said automated processing machine comprising:
    an output device for outputting slides that have been processed by the automated processing machine, said output device including an extensible and retractable drawer unit;
    an electric drive for moving the drawer unit in and out;
    a control unit for controlling the electric drive; and
    a control element connected to the control unit such that operation of the control element causes the drawer unit to move in or out; wherein
    the control unit is configured to allow the drawer unit to be moved in or out only at appropriate points in time.

12. The automated processing machine of claim 11, wherein said output device includes an extensible and retractable drawer unit that can be folded away.

* * * * *